US012640236B2

(12) United States Patent
Perry et al.

(10) Patent No.: US 12,640,236 B2
(45) Date of Patent: May 26, 2026

(54) DNA CANVAS FOR INFORMATION STORAGE AND NANOFABRICATION

(71) Applicant: Massachusetts Institute of Technology, Cambridge, MA (US)

(72) Inventors: Eyal Perry, Tel Aviv (IL); Junichi Ogawa, Tokyo (JP); Joseph M. Jacobson, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1185 days.

(21) Appl. No.: 17/317,204

(22) Filed: May 11, 2021

(65) Prior Publication Data

US 2021/0350879 A1     Nov. 11, 2021

Related U.S. Application Data

(60) Provisional application No. 63/023,155, filed on May 11, 2020.

(51) Int. Cl.
*G16B 50/30*          (2019.01)
*B01J 19/00*          (2006.01)
          (Continued)

(52) U.S. Cl.
CPC .......... *G16B 50/30* (2019.02); *B01J 19/0046* (2013.01); *G16B 30/00* (2019.02);
          (Continued)

(58) Field of Classification Search
CPC ...... G16B 50/30; G16B 30/00; B01J 19/0046; B01J 2219/00432; B01J 2219/00529;
          (Continued)

(56) References Cited

U.S. PATENT DOCUMENTS

| | | | |
|---|---|---|---|
| 2011/0226733 A1* | 9/2011 | Zu | C07C 323/60 |
| | | | 216/37 |
| 2020/0193301 A1* | 6/2020 | Roquet | G16B 25/20 |

OTHER PUBLICATIONS

Markowitz, David; 2018; IARPA Molecular Information Storage Program, 61 pages.
Rutten, Martin GTA, et al., "Encoding information into polymers", Nature Reviews Chemistry, 2018, 2.11, 365-38.
Erlich, Yaniv, et al., "DNA Fountain enables a robust and efficient storage architecture". Science, 2017, 355.6328, 950-954.
Zhirnov, Victor et al., "Nucleic acid memory", Nature materials, 2016, 15.4, 366-370.
Grass, Robert N et al., "Robust chemical preservation of digital information on DNA in silica with error-correcting codes", Angewandte Chemie International Edition, 2017, 54.8, 2552-2555.
(Continued)

*Primary Examiner* — Larry D Riggs, II
*Assistant Examiner* — Emilie A Smith
(74) *Attorney, Agent, or Firm* — Husch Blackwell

(57) ABSTRACT

A DNA canvas comprising a plurality of uniquely-coded polymer strands immobilized on a substrate can be used to provide a reference map comprising a set of reference association polymers having a dual-barcode generated by nondestructively associating spatially-adjacent polymers on the DNA canvas, encoding digital information on the DNA canvas to provide a patterned DNA canvas by disabling a pattern of selected plurality of polymers strands to provide a set of data association polymers having a single bar code that corresponds to a single bit in the bitmap. The digital information capable of being retrieved by sequencing the set of reference and data association polymers, computationally recovering spatial locations of each of the selected polymer strands that were disabled and recovering the bitmap encoded in the pattern of disabled polymer strands by comparison of the set of reference association polymer sequences to the set of data association polymer sequences.

18 Claims, 8 Drawing Sheets

(51) Int. Cl.
  *G16B 30/00* (2019.01)
  *C12Q 1/6869* (2018.01)
(52) U.S. Cl.
  CPC ............... *B01J 2219/00432* (2013.01); *B01J 2219/00529* (2013.01); *B01J 2219/00596* (2013.01); *B01J 2219/00608* (2013.01); *B01J 2219/00722* (2013.01); *C12Q 1/6869* (2013.01)
(58) Field of Classification Search
  CPC .... B01J 2219/00596; B01J 2219/00608; B01J 2219/00722; C12Q 1/6869; C12Q 1/68; C12Q 2537/165; C12Q 2563/185; G11C 13/0019
  See application file for complete search history.

(56) References Cited

OTHER PUBLICATIONS

Church, George M, et al., "Next-generation digital information storage in DNA", Science, 2012, 337.6102, 1628-1628.

Shipman, Seth L et al., "CRISPR-Cas encoding of a digital movie into the genomes of a population of living bacteria", Nature, 2017, 547.7663, 345-349.

Stayton, Patrick S., et al., "Streptavidin-biotin binding energetics", Biomolecular engineering, 1999, 16.1-4, 39-44.

Boulgakov, Alexander A., et al., "From space to sequence and back again: iterative DNA proximity ligation and its applications to DNA-based imaging", BioRxiv, 2018, 470211, 24 pages.

\* cited by examiner

DNA CANVAS FOR INFORMATION STORAGE AND NANOFABRICATION

CROSS-REFERENCE TO RELATED APPLICATION

The present application claims the benefit of U.S. Provisional Application No. 63/023,155, filed May 11, 2020, which is hereby incorporated in its entirety by reference.

FIELD OF INVENTION

The present disclosure relates to data storage, and more particularly relates to large scale data storage using biomolecules, and a method of amplifiable data storage.

BACKGROUND

There is currently great interest in the ability to programmably pattern both bits and atoms at the nanoscale (<<100 nm) at both high speed and low cost. Such a technique is useful for a range of applications, including, but not limited to, information storage and device nanofabrication.

In the field of information storage, humanity is producing data at exponential rates. At present, exabyte-scale data storage centers require large warehouses, consume megawatts of power, and cost billions of dollars to operate over their lifetimes [Markowitz, David; 2018; IARPA Molecular Information Storage Program]. Recent studies have illustrated the potential use of molecular media, prominently DNA, to store data [Rutten, Martin GTA, et al., "Encoding information into polymers", Nature Reviews Chemistry, 2018, 2.11, 365-381]. DNA serves as an attractive storage option due to its extreme volumetric density (theoretical limit 215 PB/g [Erlich, Yaniv, et al., "DNA Fountain enables a robust and efficient storage architecture". Science, 2017, 355.6328, 950-954]), low maintenance energy (108 times more efficient than flash memory [Zhirnov, Victor et al., "Nucleic acid memory", Nature materials, 2016, 15.4, 366-370]), and long retention period (e.g. millennia [Grass, Robert N et al., "Robust chemical preservation of digital information on DNA in silica with error-correcting codes", Angewandte Chemie International Edition, 2017, 54.8, 2552-2555]). Recently, DNA has been used to accurately store digital data such as texts, images, and movies [Church, George M, et al., "Next-generation digital information storage in DNA", Science, 2012, 337.6102, 1628-1628; Shipman, Seth L et al., "CRISPR-Cas encoding of a digital movie into the genomes of a population of living bacteria", Nature, 2017, 547.7663, 345-349].

Current DNA storage methods rely on DNA synthesis to write information and next-generation sequencing (NGS) technology to retrieve data. While NGS cost is dropping exponentially, the price to synthesize base pairs of DNA has only slightly decreased over the last few decades [Markowitz, David; 2018; IARPA Molecular Information Storage Program]. Consequently, the cost of all existing DNA storage methods is higher than the cost of hard disk or flash-based storage devices by many orders of magnitude.

Similarly, in the field of nanofabrication of electronic devices, there is great interest in the ability to fabricate nano-scaled (<<100 nm) devices both cheaply and rapidly. Thus, there is a need for robust, cost-effective information storage systems that provide necessary volumetric density, low maintenance energy and long retention periods.

SUMMARY

The present disclosure generally relates to a DNA canvas for information storage and nanofabrication. The term "DNA canvas" refers to a plurality of uniquely-coded polymer strands, e.g. DNA oligonucleotides, positioned with known coordinates on a substrate at nanoscale (<<100 nm) resolutions. These uniquely-coded polymer strands, referred to as array polymers, may be used as bits in an information storage system or as assembly points in the fabrication of a nanodevice.

In some aspects, a DNA canvas is used for a method of storing information. The method can comprise (i) providing a DNA canvas, wherein the DNA canvas comprises a plurality of polymer strands immobilized on a substrate at a known coordinate, each of the plurality of polymer strands uniquely coded; (ii) conducting iterative proximity ligation on each pair of adjacent polymer strands to provide a reference map of the DNA canvas, the reference map comprising dual-barcoded DNA strands from each adjacent polymer strands on the DNA canvas; (iii) writing a bitmap encoding digital information on the DNA canvas to provide a patterned DNA canvas, wherein the patterned DNA canvas comprises at least one non-irradiated polymer strand; (iv) amplifying the at least one non-irradiated polymer strand; and (v) isolating the at least one amplified non-irradiated polymer strand to provide at least one copy that defines a data map, wherein each copy contains a single barcode that corresponds to a single bit in the bitmap; (vi) drying and storing the reference map and the data map. In some aspects, the information from the reference and data maps may be retrieved. In some aspects, the retrieval process comprises (i) sequencing both the reference and data maps, and (ii) decoding the digital information from the sequenced reference and data maps.

In some aspects, the disclosure is directed to a method of storing digital information, which involves spatially arraying a plurality of array polymers, wherein each array polymer is a uniquely-identifiable polymer sequences. A set of reference association polymers is generated by nondestructively associating spatially-adjacent array polymers. The association is stored in copyable or amplifiable polymers. Data is encoded by disabling a pattern of a selected plurality of array polymers. A set of data association polymers is generated by nondestructively associating spatially-adjacent non-disabled array polymers in which the association is stored in copyable or amplifiable polymers. Computationally recovering spatial locations of disabled array polymers and recovering the data encoded in the pattern of disabled array polymers by comparison of the set of reference association polymers to the set of data association polymers.

In some aspects, each array polymer comprises a polynucleotide. In some preferred aspects, each array polymer comprises an oligonucleotide. In some other preferred aspects, each array polymer comprises a DNA oligonucleotide having about 13 to about 200 base pairs, more preferably about 15 to about 180 base pairs, more preferably about 30 to about 150 base pairs.

In some aspects, the plurality of array polymers can be inexpensively replicated to a new system while preserving spatial locations.

In some aspects, the plurality of array polymers are spatially arrayed on a Streptavidin-coated substrate. In some aspects, each array polymer comprises a Biotin attachment.

In some aspects, the plurality of array polymers comprise a ratio of Biotin attachments and polynucleotides synthesized with a Biotin attachment. In some aspects, the ratio of Biotin attachments and polynucleotides synthesized with a Biotin attachment is determined according to a desired average distance between spatially-adjacent array polymers.

In some aspects, the plurality of array polymers are replicated to a new system while preserving spatial locations by polymerase extension, Biotin attachment, and transfer to a new Streptavidin-coated substrate.

In some aspects, disabling of array polymers is carried out by means of direct optical degradation of the polymer. In some aspects, disabling of array polymers is carried out by means of direct electron beam degradation of the polymer. In some aspects, disabling of array polymers is carried out by means of optical or electron beam lithography. In some aspects, the lithography employs a negative resist. In some aspects, disabling of array polymers is carried out by means of photocleavable or electron beam cleavable chemical group which attaches said array polymers to a substrate.

In some aspects, the recovered spatial locations of array polymers are used to build nanostructures or nanoelectronics or nanobio chips by attaching structural or electronic or biological components such as nanoparticles, nanotubes or nanowires, or proteins to a selected plurality of polymers.

In some aspects, a system for amplifiable data storage is disclosed. The system has a reference map and a data map.

Each of the reference map and the data map has a substrate uniformly coated with a first half of a binding complex and a plurality of array polymers comprising a second half of the binding complex such that the array polymers are uniformly distributed on the substrate.

Each array polymer comprises a uniquely-identifiable polymer sequence. The reference map comprises a set of reference association polymers, determined by nondestructively associating spatially-adjacent array polymers in which the association is stored in copyable or amplifiable polymers.

The data map comprises a set of data association polymers, determined by encoding of data by disabling a pattern of a selected plurality of array polymers and nondestructively associating spatially-adjacent non-disabled array polymers in which the association is stored in copyable or amplifiable polymers.

The data encoded in the pattern of disabled array polymers by comparison of the set of reference association polymers to the set of data association polymers.

In some aspects, the first half of the binding complex is Streptavidin and the second half of the binding complex is Biotin.

In some aspects, each array polymer comprises a polynucleotide. In some aspects, the plurality of array polymers can be replicated to a new system while preserving spatial locations.

In some aspects, the second half of the binding complex comprises a ratio of Biotin attachments and polynucleotides synthesized with a Biotin attachment. In some aspects, the ratio of Biotin attachments and polynucleotides synthesized with a Biotin attachment is determined according to a desired average distance between spatially-adjacent array polymers.

In some aspects, the plurality of array polymers are replicated to a new system while preserving spatial locations by polymerase extension, Biotin attachment, and transfer to a new Streptavidin-coated substrate.

BRIEF DESCRIPTION OF THE DRAWINGS

Other aspects, advantages and novel features of the invention will become more apparent from the following detailed description of the invention when considered in conjunction with the accompanying drawing, wherein.

DETAILED DESCRIPTION

The present disclosure relates to data storage, and more particularly to exabyte-scale DNA data storage.

Figure 1A:
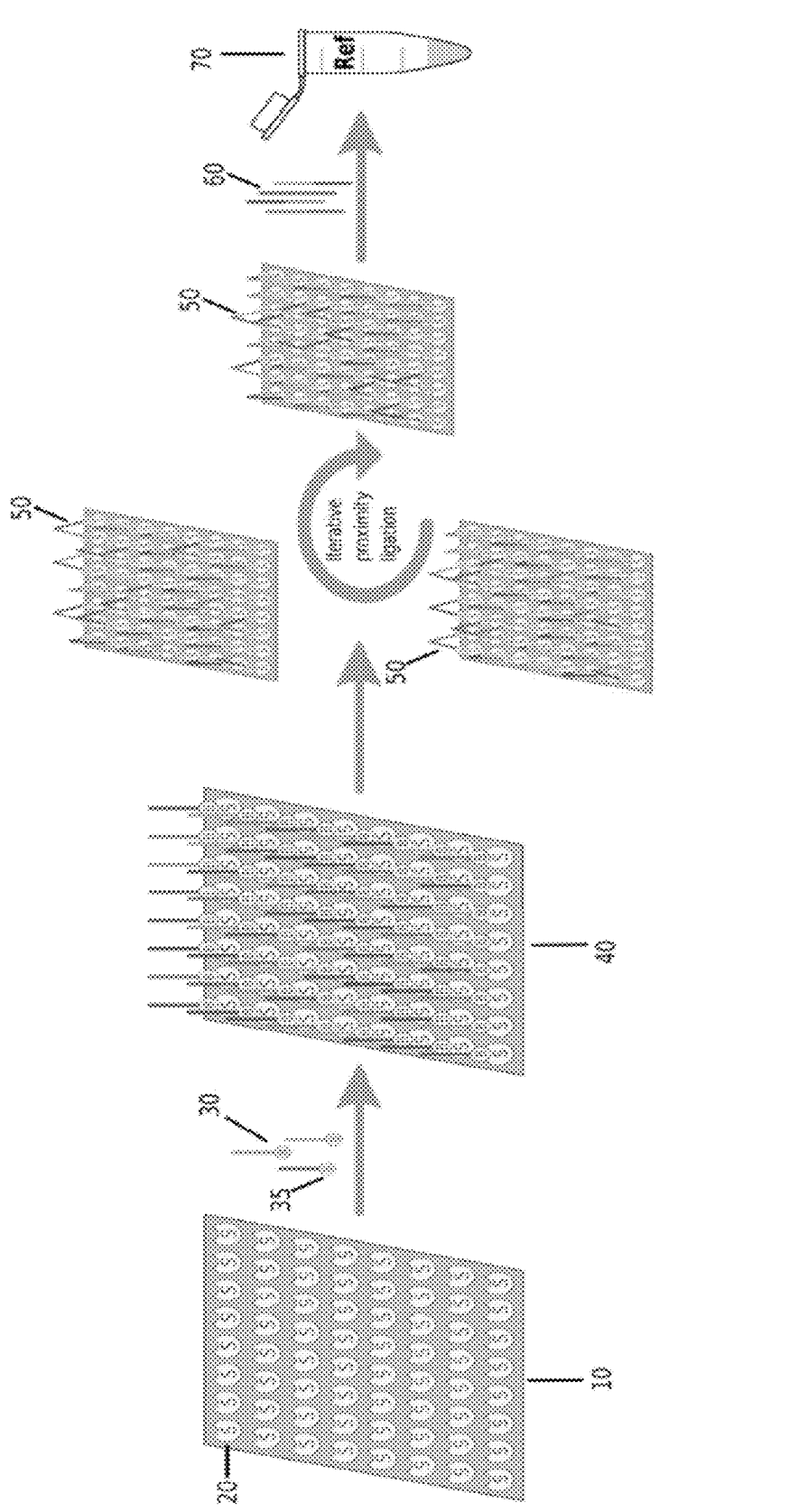
FIGS. 1A-C are diagrams that, taken together, depict an overview of an embodiment of a DNA Canvas Information Storage System according to certain aspects of the present disclosure.
Figure 1B:
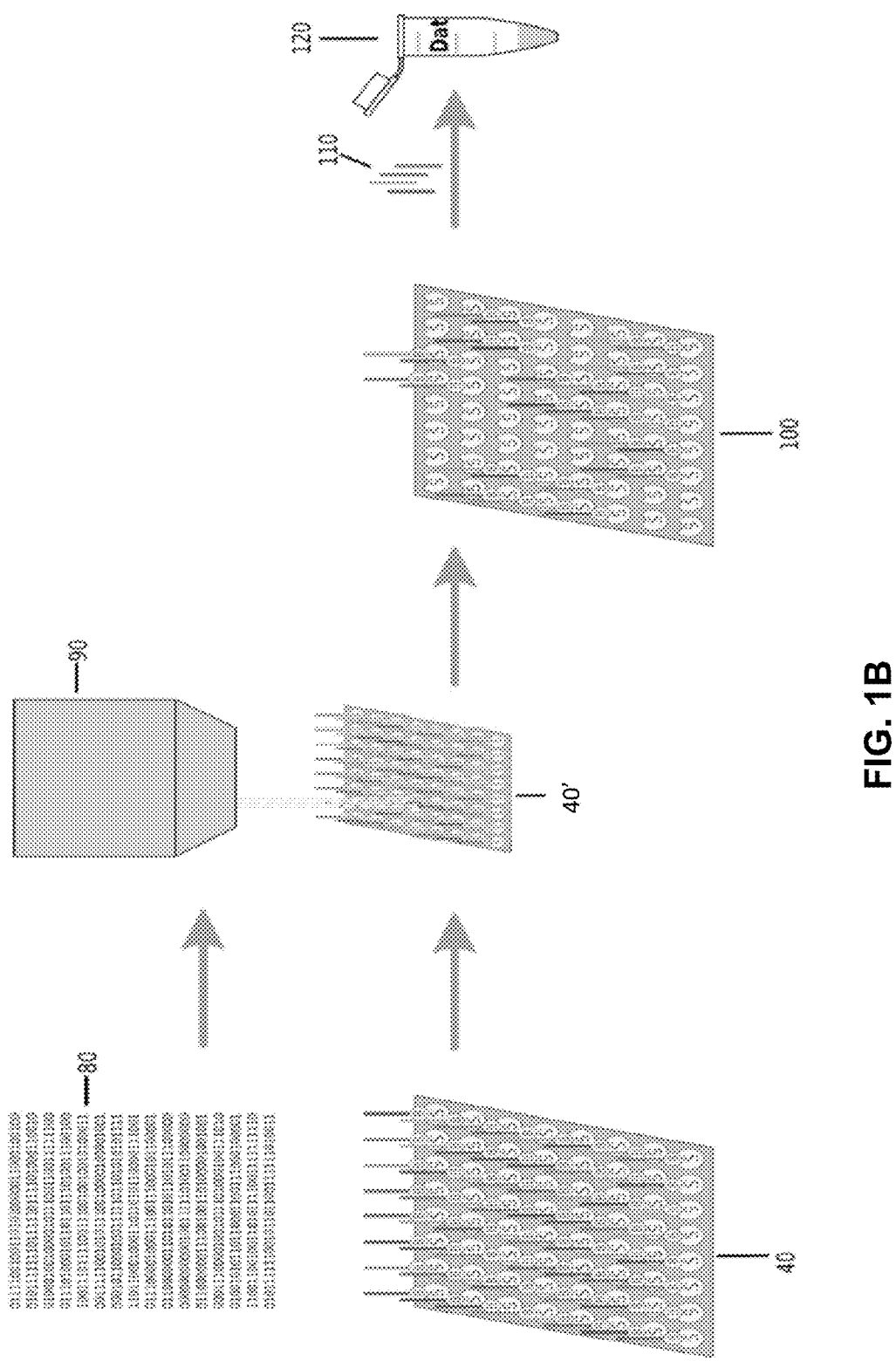
Figure 1C:
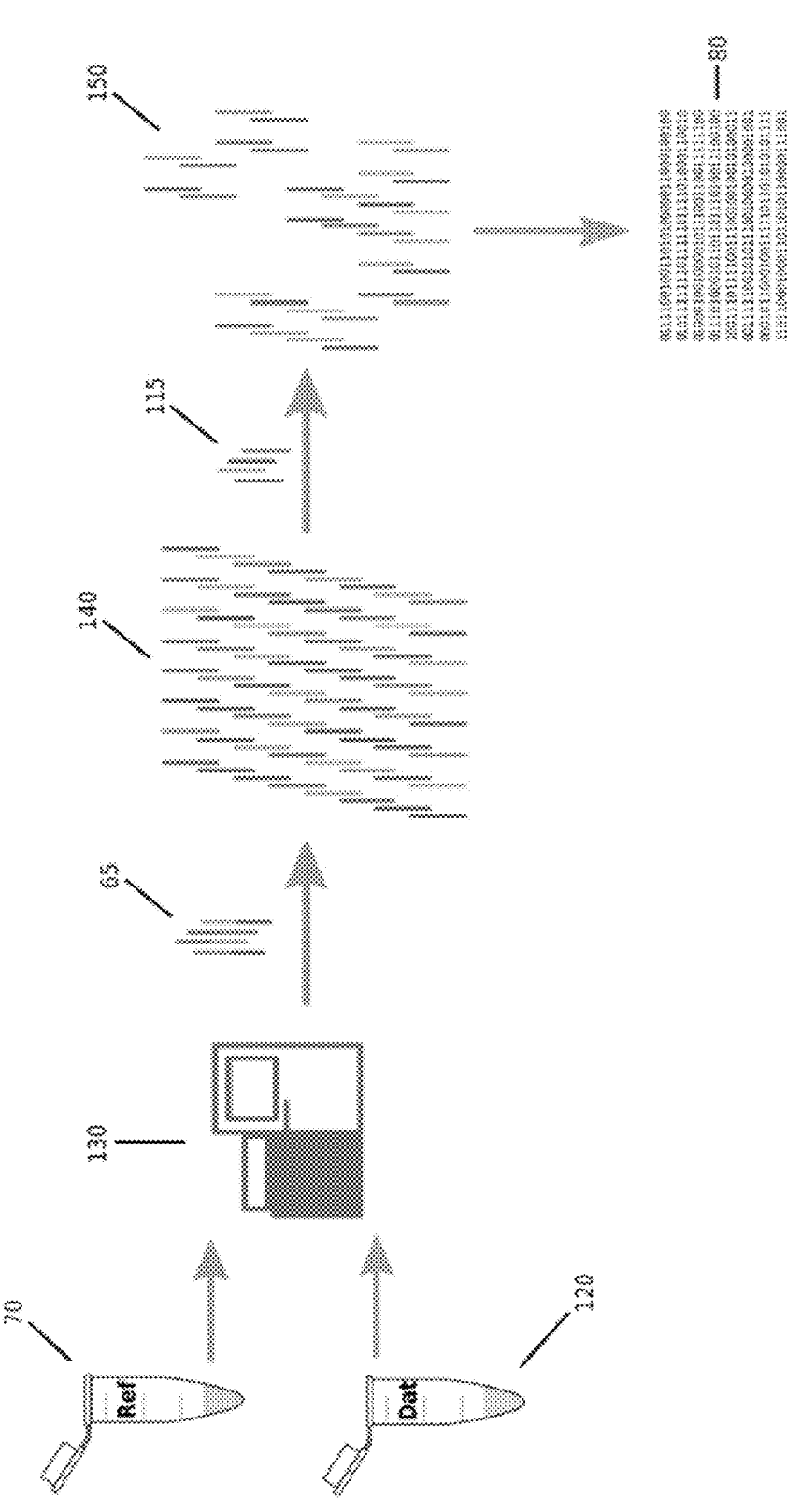

An example embodiment of the present disclosure, digital information storage using a DNA Canvas is presented schematically in FIGS. 1A-C. The first step generally comprises the preparation of a DNA canvas, as depicted in FIG. 1A, comprising a plurality of polymer strands immobilized on a substrate, and generating a reference map comprising dual-barcoded DNA strands synthesized from the DNA canvas by iterative proximity ligation. In the second step, depicted in FIG. 1B, data is written on the DNA canvas by lithography to provide a patterned DNA canvas, and generating a data map comprising single barcoded DNA strands synthesized from the patterned DNA canvas. The reference map and the data map can be stored for a desired period of time. Finally, the stored digital information is retrieved, as depicted in FIG. 1C, which includes sequencing the reference map and the data map and decoding the digital information.

Referring now generally to FIG. 1A, a DNA canvas 40 is prepared by immobilizing a plurality of polymer strands 30 to a substrate 10 at known coordinates at nanoscale resolutions. In some preferred aspects, the polymer stands 30 are uniquely-coded polymer strands, e.g. DNA oligonucleotides. In some preferred aspects, the substrate 10 comprises a glass material or a polycrystalline diamond material. In some aspects, the substrate 10 comprises a polycrystalline or single crystal material, such as sapphire, quartz, zirconia, diamond or a metal oxide. In some other aspects, the substrate 10 comprises a plastic material, such as an amorphous polymer, thermoplastic polymer or a polymeric organosilicon compound. In some aspects, the substrate 10 is a plastic material chosen from a cyclic olefin copolymer, polycarbonate, poly(methyl methacrylate), and polydimethylsiloxane.

The plurality of polymer strands 30 can be immobilized onto the substrate 10 by a binding complex formed between a coating 20 on the substrate 10 and a functional group 35 bound to each of the polymer strands 30. In some aspects, the substrate 10 is coated with a functionalized coating 20 chosen from Streptavidin, Epoxysilane, Aldehydesilane, Azide and Alkyne. In some aspects, the polymer strands 30 have a functional group 35 chosen from biotin, amine, thiol, alkyne, and azide. In some preferred aspects, the substrate 10 is coated with Streptavidin and the polymer strands 30 contain a Biotin group to form a Streptavidin-Biotin complex 20, 35 between the substrate 10 and polymer strands 30. In some other preferred aspects, the substrate 10 contains an Epoxysilane coating and the polymer strands 30 is Amino-modified to form an Amino-Epoxysilane complex 35, 20 between the substrate 10 and polymer strands 30.

In some other aspects, the polymer strands 30 can be directly immobilized onto the substrate 10 by SN$_2$ reaction or UV irradiation. In some preferred aspects, the polymer strands 30 are directly immobilized onto the substrate 10 by SN$_2$ reaction or UV irradiation, whereby the substrate 10 is a non-modified polymer chosen from cyclic olefin copolymer (COC), poly (methyl methacrylate) (PMMA), poly (dimethylsiloxane) (PDMS), polycarbonate (PC), polystyrene and poly(ethylene terephthalate) (PET). In some other aspects, the substrate 10 is modified polymer, whereby the polymer is amine-modified or copolymerized using thiol-, amino- or acrylamide ligands.

In some preferred aspects, as shown in FIG. 1A, a glass substrate 10 is uniformly coated with Streptavidin 20. Single strands (e.g., 30-200 base pair long) of oligonucleotides (oligos) 30 are synthesized with Biotin 35. A solution of oligos 30, preferably Biotinylated oligos 30 as shown in FIG. 1A, is printed over the Streptavidin-coated 20 substrate 10, such that each oligo 30 is immobilized to the substrate 10, creating the DNA canvas 40. The Streptavidin-Biotin complex 20, 35 is the strongest known non-covalent interaction between a protein and ligand [Stayton, Patrick S., et al., "Streptavidin-biotin binding energetics", Biomolecular engineering, 1999, 16.1-4, 39-44]. The strength of the Streptavidin-biotin complex 20, 35 may be preferable for ensuring the integrity of the DNA canvas 40, but any appropriate binding complex may be used.

In some alternative aspects, the coating on the substrate 10 and the functional group on the polymer strands 30 may be reversed, such as at elevated temperatures and/or specific buffers. For example, the polymer strands 30 may contain Streptavidin and the substrate 10 may contain Biotin, such that the Streptavidin-Biotin complex is still formed to immobilize the polymer strands 30 onto the substrate 10.

Several possible solutions oligos 30 can be used, including, but not limited to, a) a mixture of Biotin and Biotinylated oligos, wherein various ratios affect the average distance between neighboring oligos on the DNA canvas 40, and b) a mixture of Biotinylated oligos, for example (but not limited to) 50% with Biotin on the 5' end and 50% with Biotin on the 3' end.

Figure 2A:
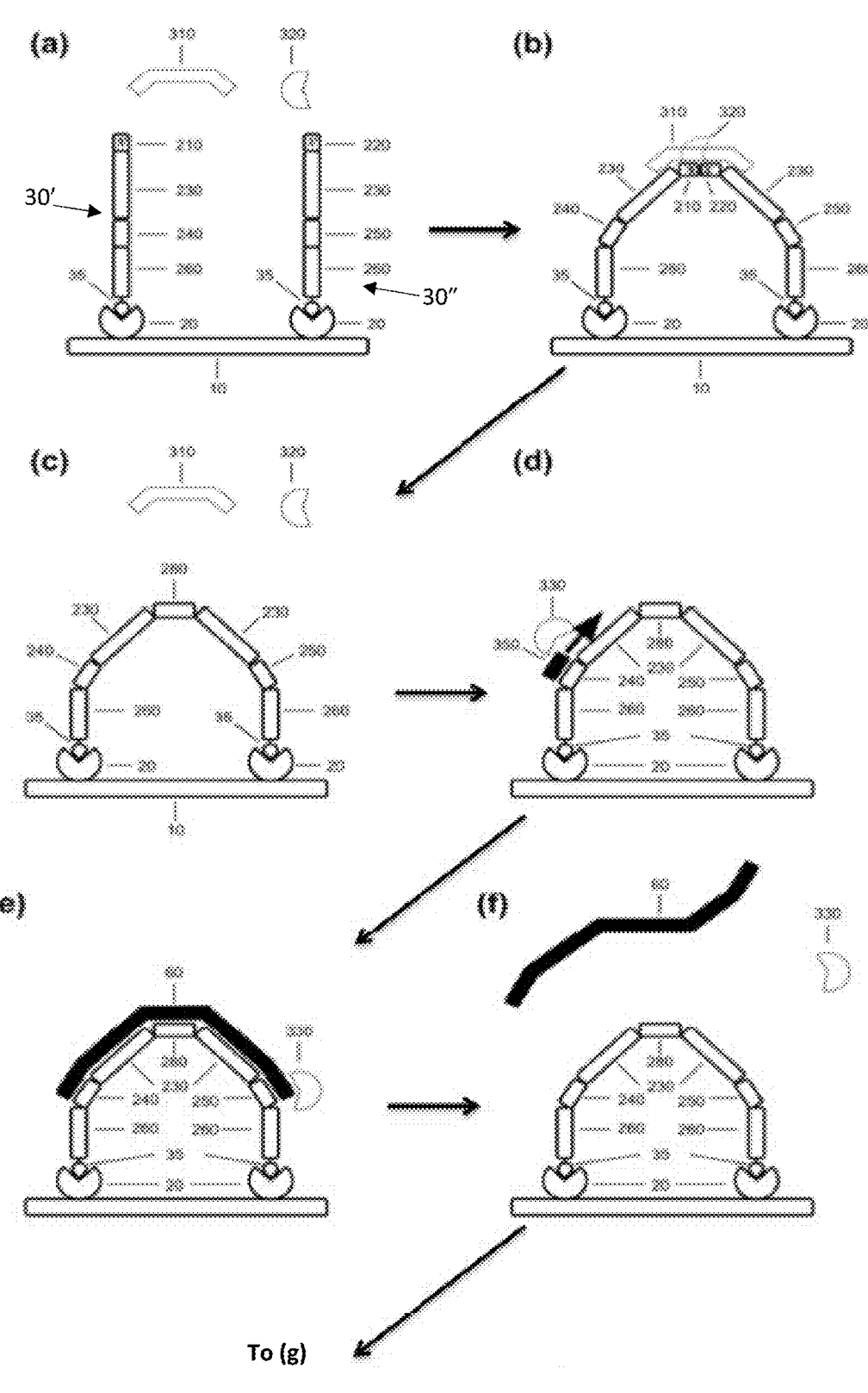
FIGS. 2A-B together comprise a diagram depicting an example of Iterative Proximity Ligation, according to one aspect of the present disclosure.
Figure 2B:
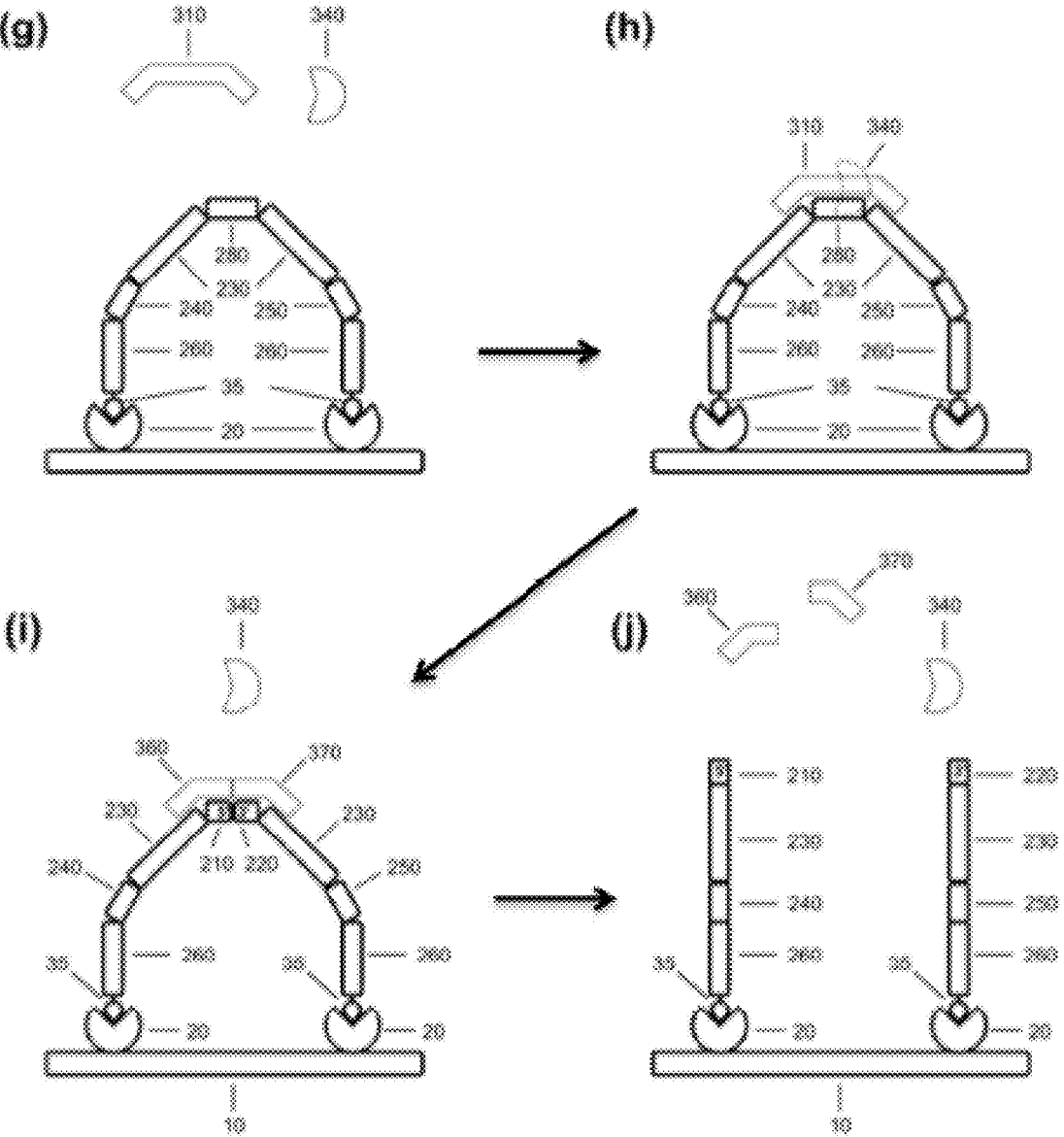

From the DNA canvas 40, a reference map 70 of the DNA canvas 40 can be generated. The reference map 70 is preferably generated by Iterative Proximity Ligation, which is depicted in FIGS. 2A-2B. As shown in FIGS. 2A-B, each oligo 30 is composed of a specially designed sequence, which can comprise a partial restriction site 210 on the 5' end of oligo 30' or a partial restriction site 220 on the 3' end of oligo 30", each of the partial restriction sites 210, 220 being used for iterative ligation, a random barcode site 230 to identify each oligo after sequencing, a forward primer sequence 240 or a reverse primer sequences 250 to facilitate synthesis by DNA polymerase 330, and a spacer sequence 260 to control oligo length. In preferred aspects, barcode site 230 of each oligo 30 contains a randomly synthesized nucleotide. The barcode length is relative to the total number of Streptavidin 20 binding sites on the DNA canvas, e.g. barcode of length twenty will have $4^{20}=10^{12}$ possible combinations. In preferred aspects, the whole oligo sequence is carefully designed to minimize self-interactions and to enable ligation between neighboring polymer strands.

Figure 5:
FIG. 5 depicts an exemplary oligonucleotide sequence, according to certain aspects of the present disclosure.

An exemplary oligo sequence is shown in FIG. 5. The oligo sequence contains a partial restriction site 210, which supports ligation between neighboring oligos. The oligo sequence also contains barcode site 230, which is specifically designed to have a TTT padding in order to avoid self-interactions. The oligo sequence further contains primer sequence 240, spacer sequence 260 and Biotin functional group 35.

Iterative proximity ligation [Boulgakov, Alexander A., et al., "From space to sequence and back again: iterative DNA proximity ligation and its applications to DNA-based imaging", BioRxiv, 2018, 470211] is a process where each pair of adjacent oligos, such as 30' and 30" in FIG. 2, are connected and amplified by synthesis 50. The flow for a given pair of oligos is illustrated in FIG. 2.

As shown in step (a) of FIG. 2A, an abundance of DNA connector bridges 310 is spread over the DNA canvas 40, along with DNA ligase 320. Each connector bridge 310 contains a complementary sequence to the partial restriction sites 210, 220. In step (b), DNA ligase 320 links the 5' end and the 3' end of the neighboring oligos 30', 30". In step (c), the DNA connector bridge 310 and DNA ligase 320 are melted and washed off the DNA canvas 40. In step (d), DNA polymerase 330 and primers 350 are flowed over the DNA canvas 40. In step (e), DNA polymerase synthesizes a complementary dual-barcoded DNA strand 60 corresponding to the two adjacent oligos 30', 30". In step (f), the dual-barcoded DNA strand 60 is melted and washed off to collection in a tube, named "reference map" 70. The reference map 70 contains a plurality of dual-barcoded DNA strands 60 relating to the various adjacent oligos 30', 30" of the DNA canvas 40. In step (g) shown in FIG. 2B, restriction enzymes 340 are added to the DNA canvas 40. In steps (h-i), restriction enzymes 340 cleave the bridges between the various adjacent oligos 30', 30". Finally, in step (j), the cleaved connector bridge and restriction enzyme are washed away providing the DNA canvas 40 in the same condition prior to generating the reference map 70. The whole process of steps (a)-(j) can be repeated multiple times, thus allowing each oligo 30 to link to every neighbor oligo 30 in its vicinity. At the end of these process steps, the DNA canvas 40 is substantially provided in its original condition and reference map 70 contains at least one dual-barcoded DNA strand 60, preferably a plurality of dual-barcoded DNA strands 60, corresponding to each adjacent pair of oligos 30 on the DNA canvas 40.

After the reference map 70 is generated, data can be written on the DNA canvas 40. Referring now to FIG. 1B, data is written on the DNA canvas 40 preferably by lithography. First, the digital information to be written on the DNA canvas 40 is encoded as a bitmap 80, preferably a binary bitmap 80. Error correction schemes can be utilized to ensure robustness to errors in the write/read processes. Since reconstruction of the binary bitmap 80 is invariant to rotations and reflections, the bitmap 80 can be enclosed within a contour which is distinct under such operations. Alternatively, unique shapes can be embedded with the bitmap 80 in known locations to ensure reconstruction accuracy.

Lithography technology is preferably utilized to pattern the DNA canvas 40 to provide a patterned DNA canvas 40'. This can be accomplished by covering the DNA canvas 40 with a resist layer. Then, the bitmap 80 is written over the resist coated DNA Canvas using a lithography machine 90. Here, high throughput maskless lithography technology that directly writes the bitmap pattern 80 onto the DNA canvas 40 is utilized. For example, a UV direct photolithography system, such as, but not limited to, Heidelberg MLA-150 or electron-beam lithography system, FlexSEM 1000 may be used.

In certain preferred embodiments, glass is a suitable base material or substrate 10 of the DNA canvas 40, in terms of its ability to be coated with Streptavidin and retain the protein. In certain aspects, charge-up when the electron-beam lithography technology is used for the patterning may be a concern, because the glass substrate 10 is an insulated material. To avoid this charge-up problem, environmental SEM mode may be employed. In this mode, a low vacuum state is maintained in the chamber during the beam irradiation, and environmental molecules such as nitrogen gas, oxygen or water absorb excess charge on the substrate 10. As a result, damage to the substrate 10 is minimized and the patterning resolution is kept as high as possible. In certain aspects, the pressure in the chamber is controlled to be about 6 Pa to about 100 Pa. In the case of UV direct photolithography systems, any patterning is possible with no issues, even if the substrate 10 is insulating.

The writing process is designed to avoid damage to any other components, such as the glass substrate 10, the proteins, and the DNA strands. To accomplish this, the type of resist needs to be considered. Since the DNA strand is damaged by UV or electron-beam irradiation, a negative tone resist is preferred over a positive tone resist.

When the negative tone resist system is used, the irradiated place will be polymerized and the resist remains onto the oligos 30 after the developing process. The oligos 30 under the polymerized resist will not be contributed to synthesis by the polymerase reaction. After development, a single copy of the connected oligos can be synthesized by polymerase reaction without any irradiation damage. Furthermore, an alkaline environment has the potential to dissociate the Biotin-Streptavidin interaction. Therefore, a pH neutral developer is suitable. IN some preferred aspects, SU-8 resist is one of many candidates meeting the aforementioned considerations.

The remaining non-irradiated oligos 100 are amplified using DNA polymerase and isolated after a melting reaction. The last step is repeated several times to ensure an ample amount of copies 110 of each non-irradiated oligos 100. The copies 110 are stored as the data map 120. Each copy 110 contains a single barcode that corresponds to a single bit in the bitmap 80.

The reference map 70 and data map 120 can each be dried and stored for a millennium [Grass, Robert N et al., "Robust chemical preservation of digital information on DNA in silica with error-correcting codes", Angewandte Chemie International Edition, 2017, 54.8, 2552-2555].

Figure 3:
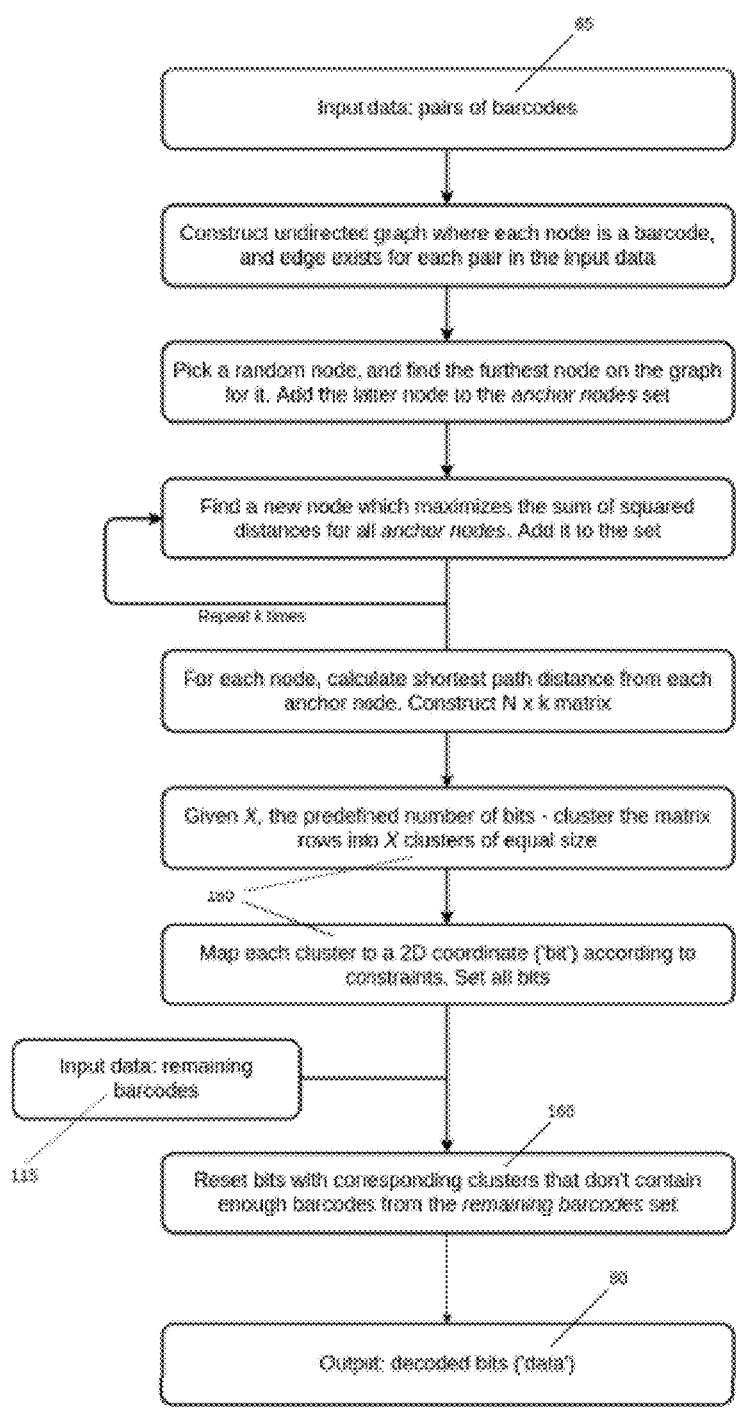
FIG. 3 is a flowchart of an example Decoding Algorithm, according to one aspect of the present disclosure.

The information contained in reference map 70 and data map 120 can also be retrieved. The information retrieval process is depicted in FIG. 1C, with a flowchart of an example decoding algorithm being shown in FIG. 3. First, as shown in FIG. 1C, both the reference maps 70 and the data map 120 each need to be sequenced to provide reference sequences and data sequences. In some preferred aspects, the sequencing is conducted using a next-generation sequencing (NGS) machine 130.

The reference sequences are composed of barcode pairs 65 corresponding to adjacent oligos on the DNA canvas 140. Computationally, an undirected graph is constructed where a node corresponds to a barcode and an edge between two nodes exists if and only if a copy of the corresponding barcode pair was sequenced. Given enough barcode pairs, the graph becomes fully connected. Then, a clustering algorithm assigns each node to a cluster 160 that corresponds to a region in the bitmap. The algorithm leverages prior information, such as the known total number of bits and the unique embedded contour/shapes. Lastly, the sequences 115 from the data map are used to calculate which clusters 160 are on or off to provide the patterned DNA canvas 150, which provides the decoded digital information 80.

Figure 4:
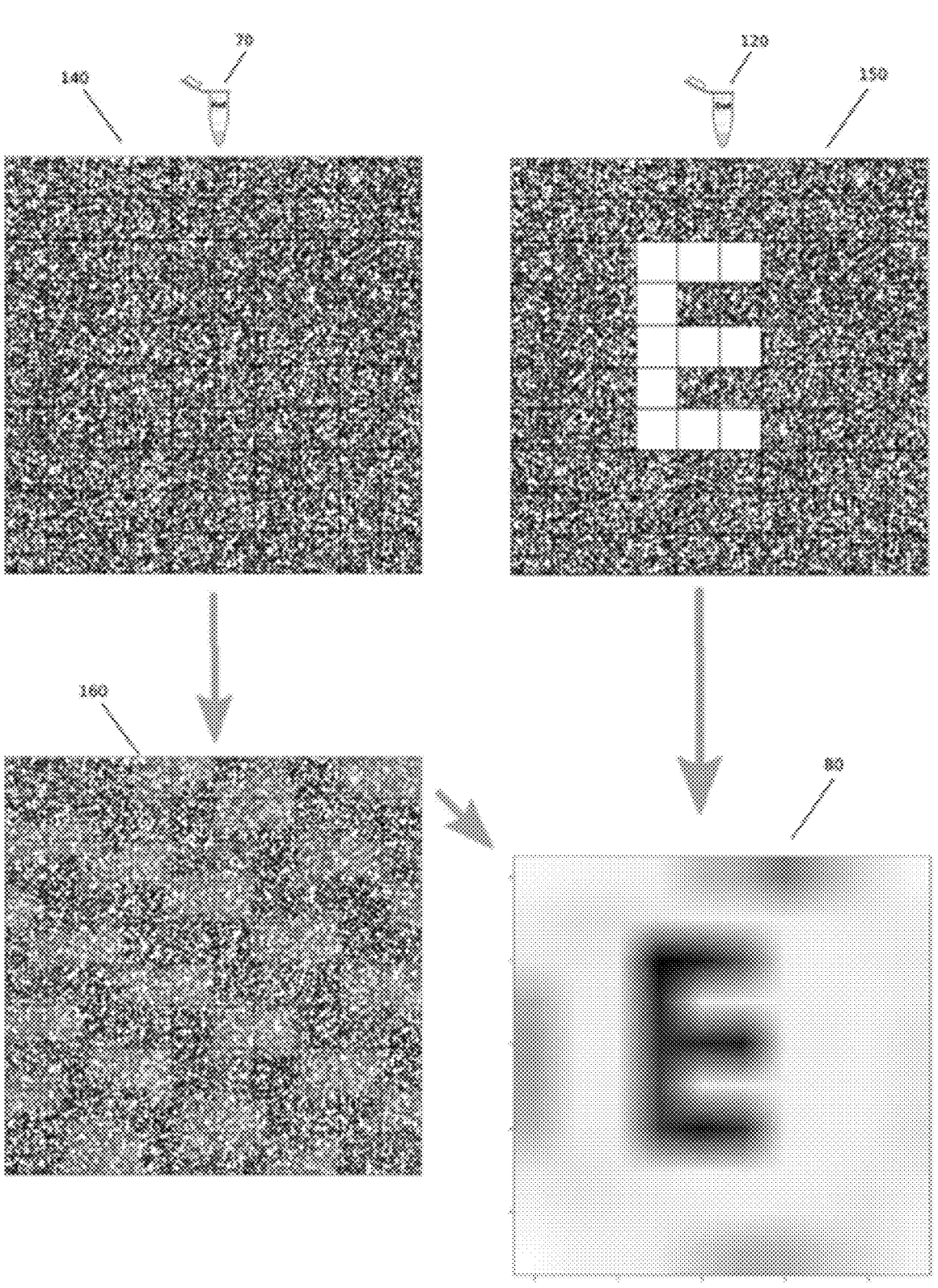
FIG. 4 depicts illustrative results from a computer simulation of encoding and decoding digital information, according to certain aspects of the present disclosure.

FIG. 4 depicts illustrative results from a computer simulation of encoding and decoding according an embodiment of the present invention. Parameters for the simulation of FIG. 4 include Storage capacity: 100 bits, Chip area: 4 μm 2, Number of DNA barcodes: 28,000, and ND DNA probe length: 100 basepairs. The reference map 70 can be used to re-generate the DNA canvas 140, the data map 120 can be used to re-generate the patterned DNA canvas 150, and the sequences 115 from the data map are used to calculate which clusters 160 are on or off to provide the patterned DNA canvas 150, which provides the decoded digital information 80.

The DNA canvas 140 can be inexpensively replicated while preserving barcode identities and spatial locations. Each oligo 30 can be immobilized to the original substrate 10 using Biotin-Streptavidin on the 5' end or 3' end. For oligos 30 that are attached at the 3' end, Biotinylated-DNA extension strands which are complementary are hybridized to the 5' end 210. Next, DNA primers 350 and DNA polymerase 330 are used to extend the complementary strand, and DNA ligase 320 is used to link the Biotinylated extension. For oligos 30 that are attached at the 5' end, Biotinylated-DNA primers are hybridized to the 3' end and DNA polymerase 330 is used to extend the complementary strand. The DNA canvas 40 is now composed of rigid double stranded DNA, with Biotin attached on the far ends from the substrate. A new glass substrate 10 coated with Streptavidin 20 is now attached over the original DNA Canvas. Streptavidin-Biotin complexes are formed on the new substrate. Lastly, the double stranded DNA is melted off to single-stranded oligos and the new DNA Canvas is lifted off.

Tables 1 and 2 tabulate Amortized Write/Read Costs for the present invention. In Table 1, Write cost is calculated by adding the costs of the reagents (oligonucleotides) per bit to the cost of the machine per bit. To calculate the cost of the machine, the machine (Heidelberg MLA-150) cost is amortized over five years and the time to write a single bit is calculated. The total cost per Gigabit is less than one dollar.

TABLE 1

| Machine cost | 1,000,000.00 $ | |
| --- | --- | --- |
| Machine cost arrortized (over 5 | 22.83 | $/hour |
| Bit size (machine resolution) | 1.00 | 1 Jm'"2 |
| Wafer size (diameter) | 6.00 | inch |
| Bits per wafer | 18.24 | Gbit |
| Write time per wafer | 25.00 | rrinute |
| Biotinylated oligos cost | 15.00 | $/nrrole |
| Oligos per bit | 0.02 | nrrole/Gbit |
| Oligos cost per bit | 0.35 | $/Gbit |
| Write time per bit | 1.37 | rrinute/Gbit |
| Write time cost per bit | 0.52 | $/Gbit |
| Total cost per bit | 0.87 | $/Gbit |

In Table 2, Read cost is calculated according to the current cost of sequencing DNA on an Illumina MiSeq Standard V3. The read cost is slightly over a hundred dollars per Gigabit.

TABLE 2

| Sequencing run cost | 2,000.00 | $/run |
| --- | --- | --- |
| Reads per run | 125.00 | M reads/run |

TABLE 2-continued

| Reads per bit (reconstruction | 1.32 | M reads/Gbit |
| Cost of a single read | 80.00 | $/M reads |
| Cost per bit | 105.38 | $/Gbit |

At least the following aspects, implementations, modifications, and applications of the described technology are contemplated by the inventors and are considered to be aspects of the present disclosure:

(1) An amplifiable data storage method comprising the steps of: Spatially arraying a plurality of uniquely-identifiable polymer sequences ("Array Polymers"); Nondestructively associating spatially-adjacent Array Polymers in which the association is stored in copyable or amplifiable polymers ("Reference Association Polymers"); Encoding of data by disabling a selected plurality of Array Polymers; Nondestructively associating spatially-adjacent non-disabled Array Polymers in which the association is stored in copyable or amplifiable polymers (hereinafter Data Association Polymers); and Computationally recovering spatial locations of Disabled Array Polymers and thus recovering the data encoded in the pattern of disabled array polymers by means of comparison of the set of Reference Association Polymers to the set of Data Association Polymers.

(2) The afore-mentioned method, wherein polymers are polynucleotides.

(3) The aforementioned method, wherein the polymers can be inexpensively replicated to a new system while preserving spatial locations, by means of polymerase extension, Biotin attachment and transfer to a new Streptavidin-coated substrate.

(4) The afore-mentioned method, wherein disabling of array polymers is carried out by means of direct optical or electron beam degradation of the polymer.

(5) The afore-mentioned method, wherein disabling of array polymers is carried out by means of optical or ebeam lithography.

(6) The afore-mentioned method, wherein the lithography employs a negative resist.

(7) The afore-mentioned method, wherein disabling of array polymers is carried out by means of photocleavable or electron beam cleaveable chemical group which attaches said array polymers to a substrate.

(8) The afore-mentioned method, wherein the recovered spatial locations of array polymers are used to build nanostructures or nanoelectronics or nanobio chips by attaching structural or electronic or biological components such as nanoparticles, nanotubes or nanowires, or proteins to a selected plurality of polymers.

While preferred embodiments of the invention are disclosed herein, many other implementations will occur to one of ordinary skill in the art and are all within the scope of the invention. Each of the various embodiments described above may be combined with other described embodiments in order to provide multiple features.

Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention.

What is claimed is:

1. A method of storing digital information, the method comprising:

providing a DNA canvas comprising a plurality of polymer strands spatially immobilized on a substrate, wherein each of the plurality of polymer strands is immobilized on the substrate at a known coordinate, and wherein each of the plurality of polymer strands comprises a uniquely-identifiable polymer sequence;

generating a set of reference association polymers by nondestructively associating each polymer strand of the DNA canvas with one or more spatially-adjacent polymer strands, wherein the nondestructive association of each pair of spatially-adjacent polymers is stored in a copyable or amplifiable polymer defining the set of reference association polymers;

encoding a bitmap of digital information on the DNA canvas, by disabling a selected plurality of polymer strands on the DNA canvas to provide a patterned DNA canvas;

generating a set of data association polymers by nondestructively associating each polymer strand of the patterned DNA canvas with one or more spatially-adjacent polymer strands, wherein the nondestructive association of each pair of spatially-adjacent polymers is stored in a copyable or amplifiable polymer defining the set of data association polymers; and storing the set of reference association polymers and the set of data association polymers.

2. The method of claim 1, wherein each of the polymer strands comprises a polynucleotide.

3. The method of claim 2, wherein the substrate comprises a coating comprising Streptavidin, such that the plurality of polymer strands are spatially immobilized on a Streptavidin-coated substrate.

4. The method of claim 3, wherein each of the polymer strands comprises a Biotin attachment, such that a Streptavidin-Biotin complex is formed between each of the polymer strands and the substrate.

5. The method of claim 2, wherein each polynucleotide comprises a random barcode site capable of identifying each polynucleotide.

6. The method of claim 1, wherein the selected plurality of polymer strands on the DNA canvas are disabled by direct optical degradation or direct electron beam degradation.

7. The method of claim 1, the selected plurality of polymer strands on the DNA canvas are disabled by optical or electron beam lithography.

8. The method of claim 7, wherein the optical or electron beam lithography employs a negative resist.

9. The method of claim 1, wherein the selected plurality of polymer strands on the DNA canvas are disabled by means of a photocleavable or an electron beam cleaveable chemical group that attaches said polymer strand to the substrate.

10. The method of claim 1, wherein the nondestructive association of each pair of spatially-adjacent polymers on the DNA canvas to generate the set of reference association polymers comprises iterative proximity ligation.

11. The method of claim 10, wherein each copyable or amplifiable polymer defining the set of reference association polymers comprises a dual-barcoded DNA strand.

12. The method of claim 11, wherein the dual-barcoded DNA strand is synthesized by flowing DNA polymerase over the DNA canvas.

13. The method of claim 1, wherein each copyable or amplifiable polymer defining the set of data association polymers comprises a single barcode corresponding to a single bit in the bitmap.

14. A system for amplifiable data storage comprising:

a reference map and a data map, wherein each of the reference map and the data map comprises:

a substrate uniformly coated with a first half of a binding complex;

a plurality of polymer strands comprising a second half of the binding complex, such that a plurality of immobilized polymer strands are uniformly distributed on the substrate at a known coordinate, wherein each of the immobilized polymer strands comprises a uniquely-identifiable polymer sequence;

wherein the reference map comprises a set of reference association polymers, each reference association polymer provided by nondestructively associating each polymer strand with a spatially-adjacent polymer strand in which the association is stored in a copyable or an amplifiable polymer;

wherein the data map comprises a set of data association polymers, each data association polymer provided by:

encoding a bitmap of data by disabling a pattern of a selected plurality of polymer strands;

nondestructively associating each non-disabled polymer strand with a spatially-adjacent non-disabled polymer strand in which the association is stored in a copyable or an amplifiable polymer;

wherein the data encoded in the data map is capable of being computationally recovered by comparison of a set of reference association polymer sequences to a set of data association polymer sequences.

15. The system for amplifiable data storage of claim 14, wherein the first half of the binding complex is Streptavidin and the second half of the binding complex is Biotin, such that each polymer strand is immobilized on the substrate by a Streptavidin-Biotin complex.

16. The system for amplifiable data storage of claim 14, wherein each polymer strand comprises a polynucleotide.

17. The system for amplifiable data storage of claim 14, wherein the plurality of polymer strands is configured to be replicated to a new system while preserving spatial locations.

18. The system for amplifiable data storage of claim 14, wherein each copyable or amplifiable polymer defining the set of reference association polymers comprises a dual-barcoded DNA strand, and wherein each copyable or amplifiable polymer defining the set of data association polymers comprises a single barcode corresponding to a single bit in the bitmap.

\* \* \* \* \*